United States Patent
Duncan

(10) Patent No.: US 11,922,258 B2
(45) Date of Patent: Mar. 5, 2024

(54) INTERACTIVE DATA SYSTEM

(71) Applicant: Douglas Malcolm Duncan, Cedar Park, TX (US)

(72) Inventor: Douglas Malcolm Duncan, Cedar Park, TX (US)

( * ) Notice: Subject to any disclaimer, the term of this patent is extended or adjusted under 35 U.S.C. 154(b) by 0 days.

(21) Appl. No.: 18/165,009

(22) Filed: Feb. 6, 2023

(65) Prior Publication Data

US 2023/0244887 A1     Aug. 3, 2023

Related U.S. Application Data

(63) Continuation of application No. 17/467,894, filed on Sep. 7, 2021, now Pat. No. 11,620,463.

(30) Foreign Application Priority Data

Dec. 7, 2020   (ZA) ................................ 2020/07586
Aug. 31, 2021  (ZA) ................................ 2021/06328

(51) Int. Cl.
| | | |
|---|---|---|
| G06K 7/10  | (2006.01) |
| G06F 21/31 | (2013.01) |
| G06F 21/62 | (2013.01) |
| G06K 7/14  | (2006.01) |
| G06Q 40/08 | (2012.01) |
| G16H 10/65 | (2018.01) |

(52) U.S. Cl.
CPC ......... *G06K 7/10366* (2013.01); *G06F 21/31* (2013.01); *G06F 21/62* (2013.01); *G06K 7/10297* (2013.01); *G06K 7/1413* (2013.01); *G06K 7/1417* (2013.01); *G06Q 40/08* (2013.01); *G16H 10/65* (2018.01)

(58) Field of Classification Search
CPC .......... G06K 7/10366; G06K 7/10297; G06K 7/1413; G06K 7/1417; G06F 21/31; G06F 21/62; G06Q 40/08; G16H 10/65
See application file for complete search history.

(56) References Cited

U.S. PATENT DOCUMENTS

| | | | |
|---|---|---|---|
| 11,295,098 B1* | 4/2022  | Thappla ............. | G06K 7/10366 |
| 11,620,463 B2* | 4/2023  | Duncan .................... | G06F 21/62 |
| | | | 235/451 |
| 2013/0317693 A1 | 11/2013 | Jefferies .................. | B60R 25/24 |
| | | | 701/31.5 |
| 2017/0008162 A1* | 1/2017 | Tsubota ................ | H04L 12/282 |
| 2017/0024945 A1 | 1/2017 | Shalev ...................... | G07C 9/27 |
| 2017/0124792 A1 | 5/2017 | Schoenfelder ..... | G07C 9/00722 |
| 2017/0140101 A1 | 5/2017 | Anderson ............. | G16H 10/65 |
| 2022/0122068 A1 | 4/2022 | Narasimhan ......... | G06Q 20/326 |

OTHER PUBLICATIONS

List of Patents or Patent Applications Treated as Related dated Feb. 6, 2023.

* cited by examiner

*Primary Examiner* — Matthew Mikels
(74) *Attorney, Agent, or Firm* — Tutunjian & Bitetto, P.C.

(57) ABSTRACT

An interactive data system in which a user, scanning a tag such as a QR-code, is directed to a destination (which may be one of a number of different destinations) which is determined by a profile of the user, which profile is established beforehand. Optionally access to a destination is also determined by an access permission which may be granted to the user. In one example a user, scanning a menu of food and beverage offerings, is directed to a choice of food and beverage which is dependent on the user's likes and dislikes, and dietary and similar factors.

13 Claims, 5 Drawing Sheets

INTERACTIVE DATA SYSTEM

CROSS REFERENCE TO RELATED APPLICATIONS

This application is a continuation of co-pending U.S. patent application Ser. No. 17/467,894 filed on Sep. 7, 2021.

BACKGROUND OF THE INVENTION

This invention relates to an interactive data system for selectively controlling access by each of a plurality of users to a plurality of destinations and, in one aspect, to the administration of data or services linked to or associated with various destinations, which relate to at least one object, animate or inanimate.

"Destination" or "Digital Destination" is used herein in a wide sense and includes data sources, online locations, applications, computer software which may perform a specific function directly for an end user, and other subject matter.

The use of QR codes is widespread. Normally a user scanning a code is directed to a URL (Uniform Resource Locator i.e., typically a web address). A development has been a dynamic QR code generator by means of which one can change the destination URL (i.e., the digital destination) without changing the code. In addition, a dynamic code can be edited because it does not contain the actual content presented to a user but a short redirection URL.

Aspects of the invention are described hereinafter with particular reference to data which relates to an automobile. This is exemplary only and is non-limiting. The principles of the invention can be applied with equal effect to the administration of data relating to any other vehicle, an aeroplane, an excavator, an electrical generator, and other movable or stationary equipment, and to the provision of a wide range of services e.g. in the medical field, in the hospitality industry, particularly restaurants, plumbing, construction or the like, which are linked to, or which are otherwise associated with, various destinations.

A substantial amount of information and data relating to a vehicle and its usage can be generated. For example, from the date of manufacture of the vehicle, such data can relate to a full technical specification of the vehicle, engine details, gearbox details, finishing and optional extras, internal upholstery details, paint colours, wheel data and the like. Other information may relate to the price of the vehicle, the seller of the vehicle, the date of purchase thereof and the purchaser's details. Further information may relate to financial aspects such as the way in which the purchase price was financed and, thereafter, to insurance, maintenance and service history. If the vehicle were to be involved in a collision then yet more information is generated.

Data which can arise during owner-usage can also be meaningful. For example, if the vehicle is a high performance vehicle or a so-called classic, then event data may also be generated. Such data may relate to participation of the vehicle in a rally or a motor race or in a classic car exhibition or competition.

Another factor is that an owner of a vehicle may have a great deal of pride in his vehicle particularly if it is of an exceptional standard or, for example, is a vintage vehicle which has been painstakingly restored.

Further data generation arises for example from non-owner usage, vehicle storage and parking processes, and even specific medical information pertaining to a driver of the vehicle—this type of data is useful if the vehicle were to become involved in a collision.

An application by Chariotz allows for a QR code on a vehicle to be scanned and thereafter, according to requirement, for a user to be directed to a particular service provider, a dealer, an event calendar, a source of spare parts or the like. It would appear that any person scanning the code is in a position to access all of the data. This is not necessarily desirable.

The aforementioned vehicle-related information is only exemplary. Similar data compilations can be assembled for other objects and for diverse services. Each data compilation can be of a substantial size and it may be difficult to access or utilise data, in a compilation, which may be of value to a given situation or to a set of unique circumstances.

One object of the present invention is to provide a system in which data of the aforegoing kind (which has been given in respect of a vehicle only by way of a non-limiting example) can be administered in a structured and, where applicable, interactive manner.

For example, in the hospitality industry a person might be presented with a menu which offers a wide range of food products and beverages. This type of menu can be made available, together with a QR code which allows a user to scan the menu using, say, a smart phone. This process simply makes the menu available via a different medium but does not otherwise assist the person to make a food/beverage choice.

Another object of the present invention is to provide an adaptive system in which each of a plurality of users, subject to various criteria, is directed to specific destinations which include specific landing pages, applications, or content. This can be for informative, control, regulatory or commercial purposes.

SUMMARY OF THE INVENTION

The invention provides a method for selectively controlling access by each of a plurality of users to a plurality of destinations, the method includes establishing for each user a respective profile which is dependent on attributes of the user, storing the profile of each user in a database, and providing a source which is associated with defined subject matter. Any user at any time is allowed to scan the source with a scanning device and, in response to such scanning, the user is directed to a destination, included in the plurality of destinations, which is determined by the user's profile and which is associated with said defined subject matter.

A user who is allowed access to a destination may then be given access to data, an application, a service or a commercial proposal, which may be uniquely linked to that destination.

Details of a user who accesses a source may simultaneously be processed by software to authenticate the user by means of recognition software which is responsive for example to biometric data, e.g., facial features, unique to the user.

The user may previously have been registered with a status or profile that controls the user's access e.g., by means of access permissions granted, or not granted, to allocated URL destinations when a source is scanned.

Data pertaining to image recognition or other criteria relating for example to an object or an artefact may previously have been loaded into a database. Thereafter a user who has been registered with a status, details of which are recorded in the database, who accesses the database may be directed to one or more destinations, uniquely linked to the user.

Such access may be contingent on access permission having been given to the user.

Compliance with the source scanning and recognition process can be implemented on a stand-alone or independent basis. Other criteria may however be employed. Optionally a user may be called upon to enter a password or to answer qualifying questions in a unique way in order to reinforce the source scanning and recognition process. Thereafter the user may be directed to a destination, an application or to information which is specific to the access permission granted to the user.

By way of example, product packaging for a particular kind of medication is registered on a database and linked to multiple variable URL destinations. A registered user can scan a source associated with the product, take a picture of the product packaging, or use another product-related technique to initiate a recognition process. The user is then granted permission which allows the user to access information that includes, for example, medical details, and indications, contra-indications, side effects etc. of the product, linked to the user's personal medical information. This helps to ensure that the product is suitable for the user and that use instructions of the product which are specific to the user are made available to the user.

"Source" is used in a broad sense herein and includes any electronically accessible mechanism from which said electronic device produces information. Typically "source" is a QR code. This however is exemplary. Other sources comprise an image which can be scanned using image recognition technology, a code carried for example by an RFID tag, a code which is accessible by means of an NFC (near field communications) technique, a barcode, or the like. The invention is described hereinafter with reference to the use of a QR code but although this is preferred it is nonetheless exemplary.

The scanning could for example take place using a communication technique such as near field communication (NFC) wherein a user would present an enabled device to a NFC receiver/transmitter (source) which, in response, transmits to the device, which is in close proximity to the NFC component, information which directs the user to a destination.

"User" can be an entity which is animate, e.g., a person, or which is inanimate e.g., an institution, a legal persona, a machine or equipment etc. In the method of the invention each user is, typically, registered or otherwise recorded as a user, a process which in certain conditions means that the user is authorised.

The method may be implemented under the control of an administrator. The administrator may be a person but typically is a computerised system. The administrator may control access by any user to any of a plurality of destinations, the activation and deactivation of applications, record permissions pertaining to active applications, record user permissions and control functioning of a processor which is adapted to match (compare) an active application permission to a user's permission and wherein, upon a match being authenticated or established, the user is directed to the active application's address.

In a particular implementation the method is used in a system for the administration of data relating to at least one object which comprises said defined subject matter, wherein the system is under the supervision of an administrator and wherein the data, according to the nature of the data, is placed into at least one category selected from a plurality of distinct categories. The system including a computer facility in which said data is stored and said source which is associated with the object and which can be scanned by a user using an electronic device and wherein, in response to such scanning, and subject to the control of the administrator, the user's profile is authenticated and responsive thereto the user is directed to a predetermined destination at which a defined application or a defined category of the data is available or accessible.

Provided the user has been assigned the requisite permission the user may then access data in at least one of said categories in accordance with said permission.

The nature of the object may be varied. The system is described hereinafter with particular reference to the object being a vehicle but this is exemplary only and non-limiting. The object may for example be a truck, a watercraft such as a boat or sailing vessel, machinery such as a diesel generator, excavator and so on. All these examples are non-limiting.

For example the method may thus be implemented in the field of vehicle technology wherein a user is associated with a defined vehicle and the user's profile is additionally based at least on attributes of the user relating to said vehicle and wherein each of said destinations is associated with vehicle related information selected from at least the following: vehicle service and maintenance data, financial information relating to the vehicle, technical details of the vehicle, insurance details relating to the vehicle, event information.

Alternatively, the object may be animate e.g., a person, an animal or the like. Another possibility is that the object may be a legal persona e.g., a club or an association. Thus, the invention is not limited by the nature of the object provided that the principles described herein can be adapted or configured for use in connection with the object.

The computer facility may be dedicated in the sense that it is provided for the purpose and offers limited access to third parties. On the other hand, in a preferred embodiment the computer facility is internet or cloud-based and the system may be accessible under those conditions under the supervision of the administrator subject to a number of principles.

The source may be uniquely associated with the object. The source may take on any one of a plurality of different forms examples of which have been given hereinbefore. An objective in this respect is that a user, when accessing the source, is directed to information which is uniquely associated with the object. Such information may also be subject to the user's status or profile, and to access permission granted to the user. The user may for example be directed to a landing page in the computer system. It is possible to make use of image recognition techniques in such user access. A preferred source is a QR (quick response) code which can be applied to the object in any appropriate way. Such a code may be unique and may therefore be uniquely related to the object. The code can be accessed, e.g., read or scanned by means of an appropriate device which may be a mobile device such as a smart phone or a tablet and the user can thereby be directed to a landing page in which interaction with the system is possible.

The administrator may be notified upon the source being scanned.

The administrator may permit a user to access data or information in one or more of the categories referred to. The degree or extent of access may depend on a setting selected by the administrator i.e., the nature of the permission granted to the user. The administrator's role in the system is significant. The administration process is preferably automatically implemented via one or more processes which execute software routines. For example, a user may be given permission to access specific data repositories or resources and the relevant means for given effect thereto may be implemented by the administrator.

"Permission" relates to the authorisation given to a user which enables the user to access specific resources such as commercial data, commercial proposals, data files, applications (computer software or programs), printers and scanners. Permission to a user may designate the type of access afforded the user. For example, a user may be permitted to view data (read only), or the user may be entitled to read, write i.e., to input data or to update the data. A critical aspect of the invention is that through the use of the scanning technique (reading of the source) possibly allied to the control function exercised by the administrator, a procedure is provided in which the profile of a user scanning the source is identified and, by drawing permission or permissions from the administrator, the user is directed to a destination, a data source or an application which the user is authorised to access.

A profile can be associated with the user. The profile may be expressed in any appropriate way using parameters or criteria selected according to requirement. For example a user may be profiled taking into account demographic data, food preferences (diet), allergies, interests, titles, age, gender, geographic location, nationality, marital status, educational qualification, occupation, hobbies or the like.

Merely by way of example in an application of the invention based on the administration of medical data, a medical service provider e.g., a medical doctor or a surgeon at a hospital scanning a QR code (source) or a facial image of a patient before surgery, is then given access to all information relating to the surgery and to the patient. A pharmacist at the hospital, scanning the same code or image, even at the same time, would be directed to data pertaining to the patient's medication requirements, doctor's approval, medical aid schemes or the like. The data made available to the pharmacist is not available to the surgeon or vice versa.

An implementation of the invention which holds significant benefit lies in an adaptation of the principles described herein to the hospitality or food industry.

For example, a chain of restaurants may make use of the adaptive technology described herein to enable a customer to access menus which may detail a large range of different dishes, deserts, beverages and so on. In respect of each offering on the menu an analysis is done in respect of ingredients, allergy ingredients, nutritional information such as calorie counts, additives, vitamin content, weight of a meal and so on. In this respect any information which may be of importance to a consumer e.g., for health or nutritional reasons, is identified and analysed. A database is maintained by the restaurant chain which itemizes the offerings on the menus and which, for each offering lists the results of the analysis.

In respect of a registered consumer or user a complementary analysis is done. This analysis profiles the user's preferences, allergy profiles, consumption requirement in respect of calories or weight and any other information which may be of value or importance to the user. The information is shared among all of the restaurants in the chain. Consequently, a consumer going to any of the restaurants in the chain can scan the menu which is presented to the user. The user is then, in response to the scanning process and in response to the data which has been referred to, directed to a destination which, in this sense, details likeable and safe menu options together with pricing.

The service described could also be used to streamline ordering processes to confirm a consumer's particular preferences selected from a menu. The service may be extended to allow a consumer to pay for chosen offerings i.e., the meal using the same application either in advance or at the time of consumption.

The method of the invention may thus be employed in diverse situations and for example the method may be adapted and implemented by a goods or services provider who establishes said plurality of destinations and who specifies a respective access permission for a designated destination, to be granted to any user to enable said user to be directed to the designated destination and wherein a user's profile is evaluated, in response to the user scanning the source, and the user is directed to the respective designated destination only if the user's profile is authenticated and the user has been granted the access permission specified for the designated destination.

A feature of the system is that an identification process executed in respect of a single code (source) directs different users (scanners) to distinct locations and data sources based on user profiles and access permissions. The identification process controls access and prevents users without the requisite permissions from gaining access to specific content data or online locations.

It is possible for all categories of information to be kept confidential. By way of example however if the object is engaged in an event then event data may be accessible to any user. On the other hand, reverting to the vehicle embodiment by way of example only, if the vehicle is involved in an accident or is damaged then insurance data pertaining to the vehicle may be accessed only by an authorised user. Another possibility, given by way of example, is that if the object is, say, a vehicle then a full service history of the vehicle may be kept in one of the categories of information. Service personnel may then be permitted to access such data and, as appropriate, to update the data detailing service procedures, parts used, time taken and billing information.

A general expression of the inventive concepts may be expressed as follows:
(a) a user scans a source which is uniquely linked to an object, a service or other subject matter;
(b) a profile (status) is established which is uniquely dependent on attributes/characteristics/properties of the user;
(c) the user profile is stored in a database or in a scanning device associated with the user;
(d) after scanning the user is directed to a destination which is dependent on the user's profile.

Additionally, the user can be given certain access permissions determined by any suitable factors chosen for the purpose such as ownership, age, interests, food preferences, financial standing, vocational or professional standing or capability and the destination in step (d) may be determined by such access permissions.

BRIEF DESCRIPTION OF THE DRAWINGS

The invention is further described by way of examples with reference to the accompanying drawings in which.

DESCRIPTION OF PREFERRED EMBODIMENTS

Figure 1:
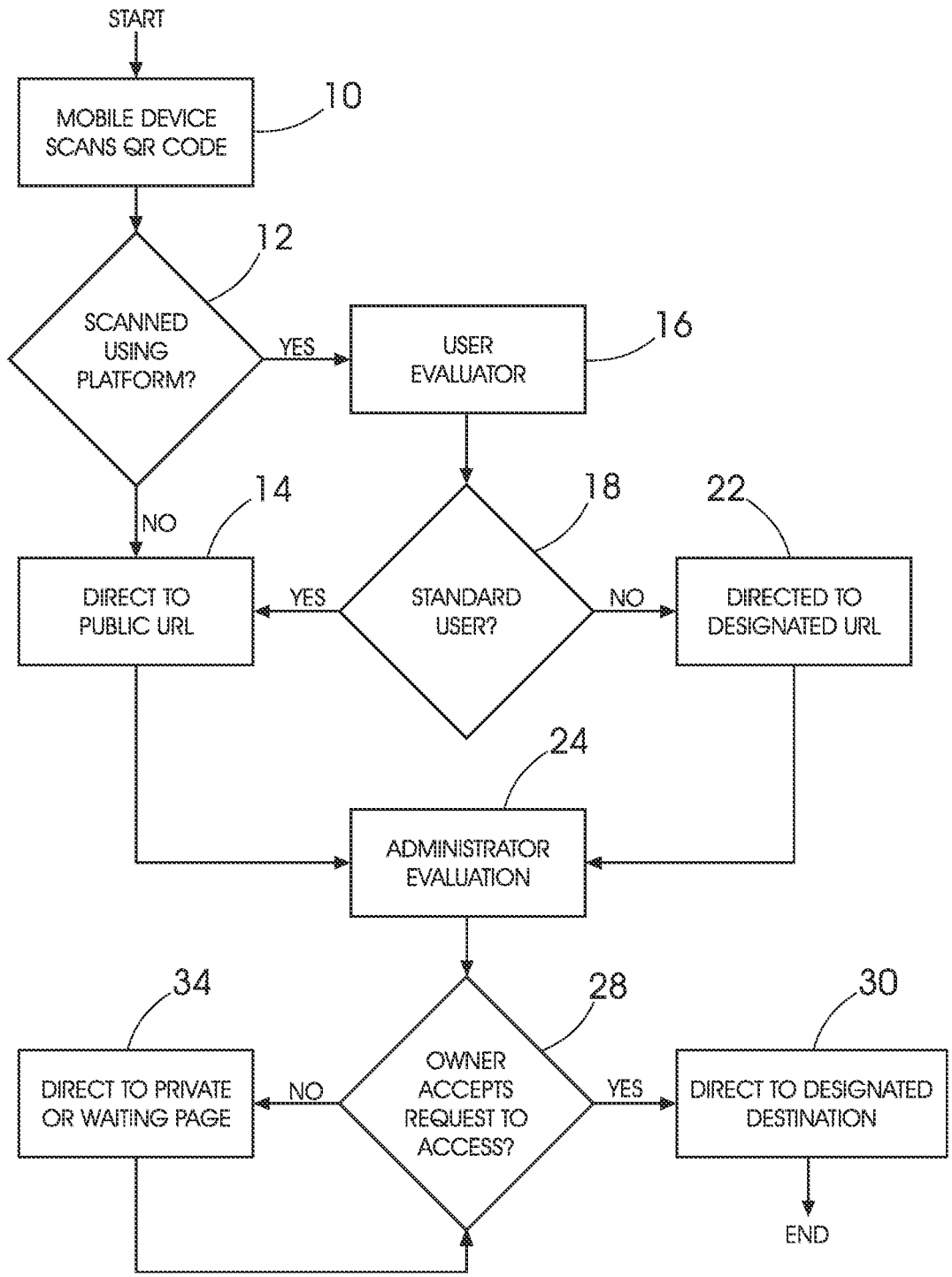
FIG. 1 is a simplified flowchart of steps in one form of the method of the invention.

FIG. 1 illustrates in broad terms the method of the invention. Assume that a QR code (also referred to herein as a "source") is assigned to an object e.g., a vehicle. A user, not shown, using a mobile device scans the code in an initial step 10. The system of the invention then determines, in a step 12, whether the scanning was implemented using the platform of the invention or not. In the latter case the user is directed to a public URL (Uniform Resource Locator) which typically is a generally accessible web page (step 14) i.e., open without restriction to the public.

If the scanning was implemented using the platform of the invention then in a step 16 the user is evaluated and in a comparative exercise 18, if it is established that user is a standard user (this typically means that the user is a member of the public and is not registered in the system) then the user is directed to the public URL—this implies that ultimately the user will not be entitled to access a designated destination.

If the user is registered in the system the user is directed to a designated URL in a step 22 which means that ultimately the user may be directed to a designated destination.

In each instance the user is evaluated in a step 24 by an administrator of the system. Typically this is done by considering a profile which has previously been drawn up for the user and which is dependent on relevant chosen features or characteristics e.g. age, interests, gender, ownership, financial standing etc. The administrator may be a person or computer software which automatically evaluates the user. The administrator (also referred to as an owner) then evaluates a request by the user to access information typically as defined hereinbefore. This is in a step 28. If the user has the requisite profile and has been accorded the requisite permission then the request is allowed and the user goes to the designated destination (step 30). If the request is refused then the user goes to a private or a waiting page (step 34)—a destination of little value.

The preceding steps have been described in connection with a single user. The method of the invention allows a plurality of users, essentially simultaneously, to scan the same code and, depending on the outcome of the role evaluation i.e., the user's profile and access permissions, to be directed to different destinations.

Normally a user is a person who would employ a scanning device such as a smart phone to interrogate the code. This aspect is however exemplary for the user could be machine- or computer-based and carry out the scanning process automatically i.e., independently of a person.

A primary benefit of the invention is that multiple users can scan the same source, i.e., code, substantially simultaneously and are then directed to different destinations depending on predetermined criteria i.e., profiles and access permissions.

Figure 2:
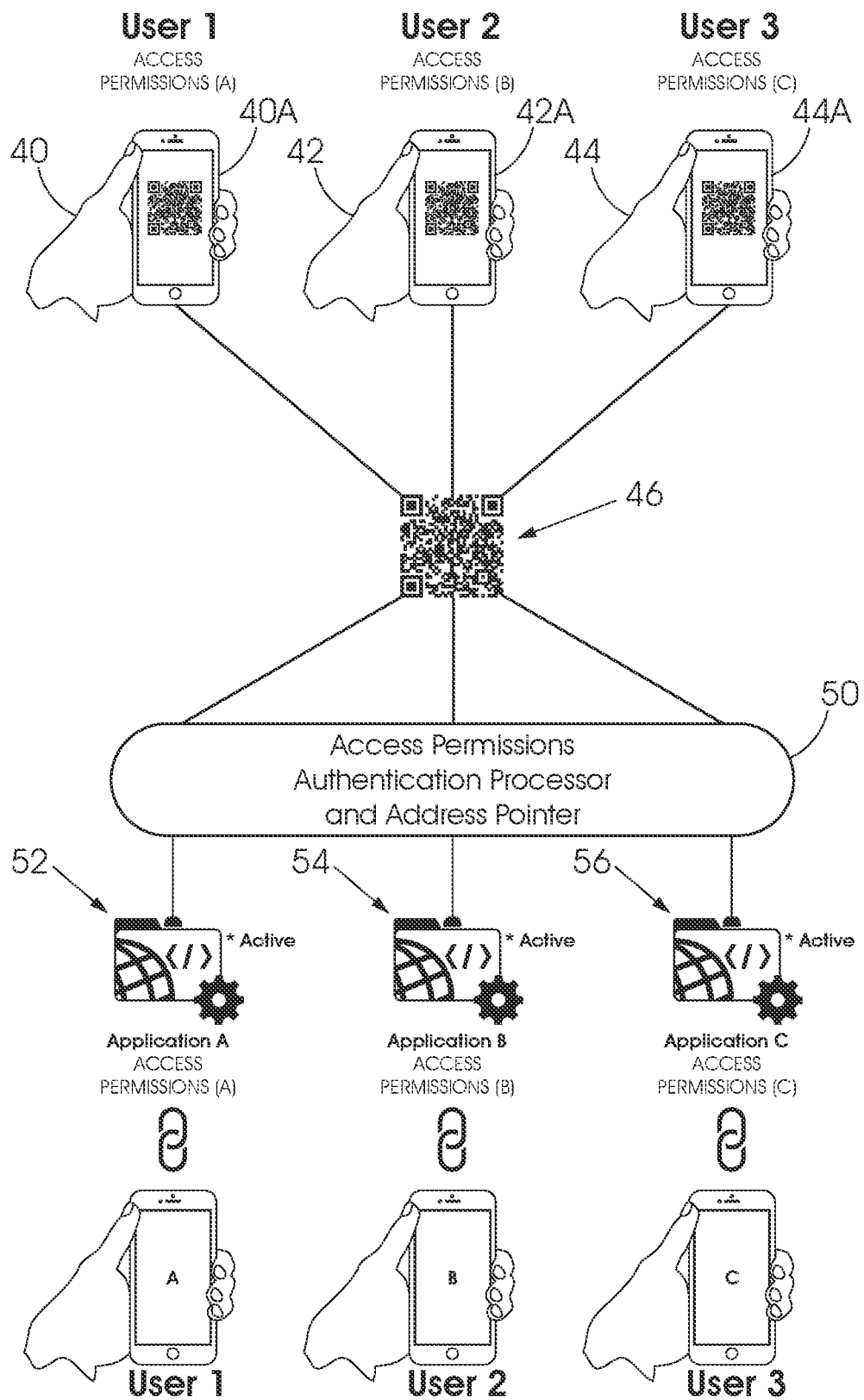
FIG. 2 is a representation of the method shown in FIG. 1 employed by multiple users.

FIG. 2 illustrates the latter aspects. Three users 40, 42 and 44 using hand-held scanners 40A, 42A and 44A substantially simultaneously scan a single code 46. Depending on the outcome of an access permission and authentication process carried out by a computer system 50 the users 40, 42 and 44 are respectively directed to destinations which enable access to respective activated applications 52, 54 and 56.

Access by individual users to specific destinations (in this case each destination is linked to a specific application) is regulated in an automated manner. This is done by directing each scanning user to information that relates to the user while employing as a control, parameters appropriate to the user, and a category of permission granted to the user.

Figure 3:
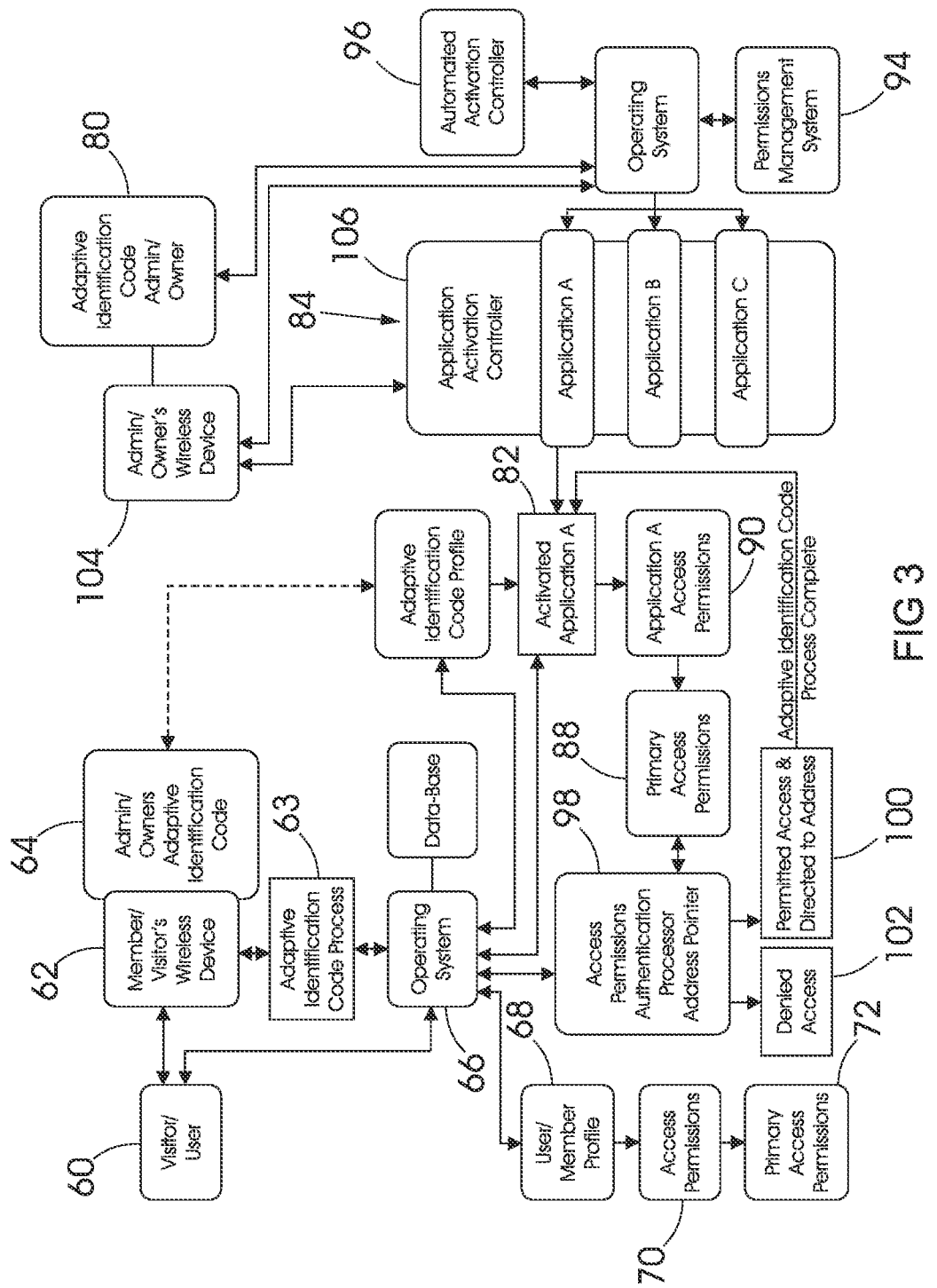
FIG. 3 is a more detailed flowchart than that shown in FIG. 1 of the method of the invention.

FIG. 3 illustrates in more detail the implementation of the method of the invention.

A user 60, registered in the system of the invention, employs a scanning device 62, such as a smart phone, to access a source 64 which typically comprises a QR code. At this time software is activated on the registered user's wireless device 62 and an adaptive identification code process 63 is enabled. The process involves the complete processing and identification of all parameters and processes used to direct the permitted user to a selected activated application.

The method runs under the control of a primary operating system 66. Stored in the system are the profiles (68) of each registered user, the access permissions profiles associated with each of the users (70) and primary access permission 72. The access permissions are access details given by an administrator 80, or generated by the operating system 66, that define access rights for accessing a specific active application 82 which is one of a plurality of applications 84 stored in inactive form.

The access permissions are updated by the system 66 to define the type of user access required for each active application 82. Profiles and permissions can be based on or determined by any of at the least following attributes or factors:

User ID
User Types: (Tier 1, Tier 2 or Tier 3)
User Application Access Types
Credit worthiness
Financial status
Food preferences
Ingredient preferences
Dietary preferences
Allergies
Location specific: Geo-location through user's wireless device
Age: Registration information on the platform
Ethnicity: Registration information on the platform
Gender: Registration information on the platform
Interests: Registration information on the platform
Hobbies
Profession
By organization, business or entity
Asset or equipment type
Financial data
Medical conditions
Personal preferences
*Wireless Device ID
Social Security Number or Government ID: For government applications
Passport Numbers
Driver's License number
Inputted Passwords (By request to access)
Inputted Passcodes. (By request to access)
Inputted One-Time-Pin. (By request to access)
Date & time
Vehicle or property ownership
Litigation record
Criminal offences Wireless device geo-fencing Payment terminal ID's (For payment applications)

Police or officer badge numbers

Government official ID's including Military ID's

Telephone numbers

Terminal or access points (i.e. VIP Parking or service crew access)

IP addresses

Activated acceptance buttons

Product Type

Product Name

Financial data

Medical conditions

A tier level is determined by usage. Thus, a person could earn points for each scanning and as the points accumulate the tier level accorded to the user changes—this value can be used as an attribute in compiling a profile for the user.

Similarly, the applications 84 are profiled by access permissions which detail parameters specific to each application. This profile enables the operating system 66 to reference and process the active applications 82 and the access permissions 88 during the execution of the identification code process 63.

The access permissions 88 within the access profile 90 are also accessible by means of a permissions management system 94, an automated activation controller 96, and the administrator 80.

The access permissions 88 define access rights for accessing a specific active application 82.

An access permissions authentication processor and address pointer 98 compares the access permission 72 of the user to the access permissions 88 of the active applications to establish matches and, upon a match, directs the user to the address of the particular active application (100). Failing a successful match, the user is denied access to any application (102). The administrator 80 is the owner, controller and manager of the activated applications 82 and inactive applications 84 and of the access permissions 88 for the applications. The administrator is capable of managing multiple identification codes within the administrator's profile. Each code is adaptive (variable) to accord with changing conditions. Control of a code may be transferrable to a new owner or to a secondary administrator.

A wireless device 104 comprises a computer or electronic scanning device with online connectivity through which the administrator 80 can control activation of the applications 84, the access permissions 88 and allow for the viewing and editing of data and content within each application.

An application activation controller 106 functions as an application activation switch and is designed to make specific applications 84 when enabled as active and subject to the requisite permission, discoverable and accessible by permitted users. The controller 106 is regulated by the administrator 80 via the device 104.

Preferably the execution of the method is automated to the maximum extent.

The inventive principles have been described in a general sense thus far. The invention finds application however in diverse situations. For example, a patient at a hospital can have a QR code associated with the patient. A surgeon scanning the code then has access to all of the necessary information pertaining to the patient's medical history and current status. A supervisor at the hospital, using a separate scanner, could then access the financial details of the patient, medical aid particulars, the contact details of next of kin and the like. Conversely the patient who may be due to undergo a particular medical procedure can himself/herself access background information and details pertaining to the procedure by scanning the patient's code or a separate code. Thus, each user is directed to a different destination dependent on the user's profile and granted permission.

Figure 4:
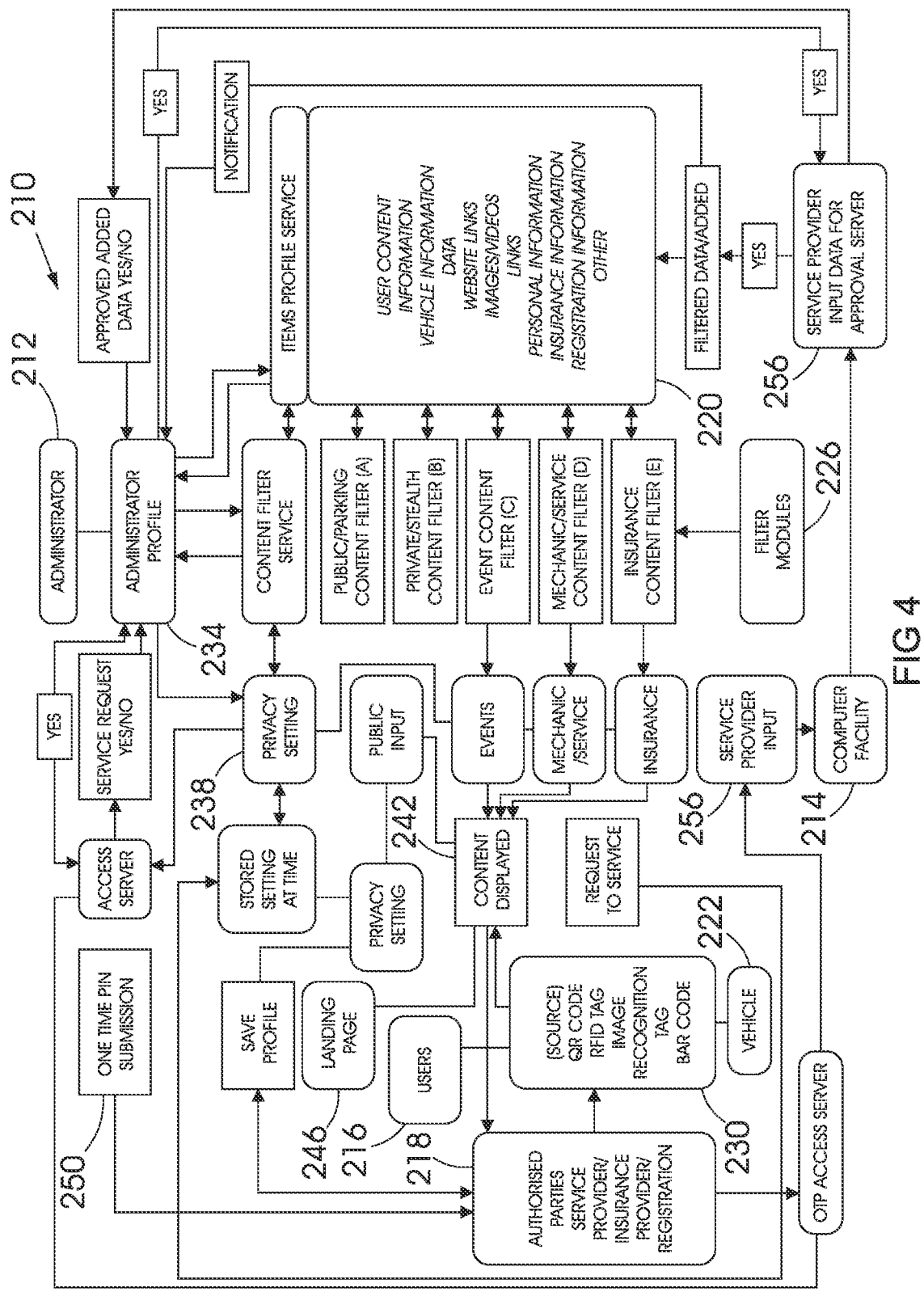
FIG. 4 depicts in flowchart form the use of the method in an interactive system for administering data relating to the vehicle.

In an explanatory implementation the method is used in an administrative system 210, shown in FIG. 4, which deals with a plurality of vehicles.

The system 210 is under the supervision of an administrator 212 and is implemented at least through the use of a computer facility 214 which may be of a dedicated nature i.e., provided for the purpose but which, preferably, is internet-based so that the system may be accessible to a broad range of users 216 or specifically authorised parties 218, and is preferably cloud-based.

The computer facility 214 includes a data storage capacity in which data 220 pertaining to a vehicle 222 is stored, and a plurality of filter modules 226, under the control of the administrator 212, to allow the data 220 to be selectively accessed according to a categorisation and filtering exercise.

The vehicle 222 has a tag 230 applied to it. The tag 230, also referred to herein as a source, is a device which is uniquely associated with the vehicle 222 and can take on any of a number of different forms. For example, the tag 230 may be an RFID tag, or a barcode. The tag 230 may also be based on image recognition technology. In a preferred and easy to implement embodiment the tag 230 is a QR (quick response) code which is generated using any appropriate software and an image of the code is then applied to the vehicle in a discrete yet ascertainable manner.

The data 220 is uniquely associated with the vehicle 222. The nature of the data is not limited and typically includes data which relates to the provenance of the vehicle i.e., the day that the vehicle was purchased, the purchase price, a full technical specification of the vehicle, details of all extras and equipment added to the vehicle and so on.

A second category of information included in the data is service history and maintenance data. Repairs to the vehicle and details of any collision in which the vehicle may have been involved etc. can also be included in this category of information.

Closely related to the aforegoing but in a distinct category is insurance information such as the quantum of insurance, details of each insurance policy, details of the insurance premiums, the name and address of the insured party, vehicle registration documentation, household drivers licenses and any other information of importance.

Another category of information, which would be of particular importance to performance and high value and classic vehicles, is event information. For example, with a performance vehicle the event information may include performance data, fuel types used, details of races in which the vehicle took part and the outcomes thereof, details of drivers and so on. For classic or vintage vehicles, particularly those which have participated in competitions, restoration and competition display information may be recorded.

The preceding description of types of data which may be included in the data 220 is exemplary and non-limiting.

The administrator 212 has a profile 234 which includes the administrator's personal details and details of the vehicle 222. The vehicle 222 may be one of a plurality of vehicles over which the administrator 212 exercises some form of control. The profile 234 may comprise a compilation of data dealing with a number of vehicles linked to the administrator 212 and, in that event, each vehicle has a respective unique QR code 230. The profile 234 can be hidden from access by ineligible users 216 (typically members of the public), or even by designated authorized parties 218 by means of a privacy setting 238 which is controlled by the administrator 212. The profile 234 could be specific to a particular vehicle 222 although, again, that profile can be set to private by the administrator 212. In that event, the administrator profile data 234 relating to the particular vehicle cannot without authorization be accessed by a third party.

Some of the information from the administrator's profile data can be included in the data 220. For example, some details of the profile can be included in the insurance information, or in the vehicle information. These aspects are under the control of the administrator 212.

The filter modules 226 are under the control of the administrator 212. The filter modules 226 detail those categories of information in the data 220 which can be accessed by a user 216, or by an authorized party 218. Five categories are indicated namely a public filter 226A, a private filter 226B, an event filter 226C, a mechanic or service filter 226D and an insurance filter 226E. The public filter 226A relates to information which in a general sense can be accessed without restriction, for example an image of a vehicle, a video of the vehicle in motion or the like. The private filter 226B is used to restrict access to the data 220 totally or to a subset thereof. Filter particulars can bear a close correlation to the permissions which are controlled by the administrator and which make up a user profile. In other words, access to a particular module is determined inter alia by the profile of the user as determined by data held at the administrator.

The event filter 226C may relate to event data such as exhibitions, race events and the like. The mechanic/service filter 226D details maintenance and service data. This data is important to ensure that a vehicle is correctly maintained and that a record is kept thereof. The data is also of great importance if the vehicle is to be sold or if it is involved in a collision or accident. This type of data can be supplemented by including information on medical facilities and personal data which could be accessed by emergency personnel e.g., in the event of an accident involving the vehicle in order to ensure that an injured passenger or driver in the vehicle is being treated medically correctly. For this type of access, the administrator would grant permission to authorized emergency service providers. The maintenance and service data may also include applications relating to diverse services or facilities such as car washing, parking garages, registration for track events and the like.

The insurance filter 226E relates to data relevant to insurance such as the value of the vehicle, authorized repair personnel, premium data and so on.

If a user 216 sees a vehicle 222, say, in a parking lot then it is possible for that person to scan the QR code 230 using a smart phone, tablet or the like. The user 216 is then directed to a landing page 240 (a URL) which is displayed on the mobile device together with a message 242 which details the privacy setting and the associated content filter derived from the administrator's profile 234. The accessing of the code 230 is detected by the computer facility 214 and the administrator 212 is notified of such access. The administrator 212 may, if so desired, change the privacy setting 238 to allow controlled access via the respective filter module (226A to 226E) to the appropriate data. This action can be taken via a mobile device, a desktop computer or can be based on date or time criteria or even, where applicable, the physical location of an event, or of the event.

A user 216 that is participating in the system may save or share particular profiles and, when doing so, the time and date of the saved content are stored. This is subject to the specific privacy setting 238 determined by the administrator 212 at the time. This process prevents a user 216 from accessing personal data and content without the authorization of the administrator 212. A profile which is saved and shared in this way in accordance with a privacy setting 238 has the consequence that all future content displayed is maintained within this privacy setting. For example, a user 216 scans the QR code 230 relating to one of the administrator's profile pages. The administrator's privacy settings are set for the public and has limited information available for public access. If the administrator 212 subsequently changes the privacy setting 238, say to bar access to insurance data, then a member of the public cannot access or see this content for such information is not in the public domain.

Assume that the administrator 212 selects the mechanic/service filter 226D. This would be done if the vehicle 222 has to be serviced or repaired. At a service center the authorized party, i.e., in this case a service provider 218, scans the tag 230 and gains access to the mechanic/service filter 226D and, in this setting, the service provider 218 can send a "request to service" to the administrator 212. In this way the service provider 218 can add applicable technical information relating to the service process carried out by the service provider such as performance testing and dyno results, details of spare parts replaced, service information and the like to the data 220.

Once a "service request" has been approved by the administrator 212 a one-time PIN 250 is generated and sent to the service provider 218. This one-time PIN 250 is entered by the service provider 218 in order to gain access to the administrator's profile within the parameters of the privacy settings 238 and filter modules 226 made available by the administrator 212, or possibly to the permissions protocol operated by the administrator. This process ensures that while the vehicle 222 is being maintained other parties cannot access the profile. For example, if a vehicle 222 is sent to a service center for maintenance purposes then while the vehicle is parked in an area which is publicly available, if a member of the public were to scan the QR code 230, that person would not be able to access any information, data or content pertaining to the mechanic/service information.

When a service provider 218 inputs data 256 to the administrator's profile the content is filtered and saved as service provider content—this allows the administrator 212 to use the filter 226D to hide or show all or some of the data 256.

As noted, if a service is being conducted on the vehicle 222 then the outcome of tests conducted by the service provider can be uploaded to a storage facility operated by the administrator. For example, a tuning center may submit dyno test results or equipment performance results to such storage. The filing of this data can be used to identify trends, solutions and problem prevention.

In broad terms the system of the invention allows for data pertaining to a vehicle to be collected, categorized and stored for controlled access in a manner which is determined by an administrator. The vehicle in question can be one of a number of vehicles which are similarly treated. Such access, in respect of a user, is also determined by the user's profile which is based on multiple selected parameters or criteria. In respect of each vehicle the nature of the data collected, stored and accessed can be determined by the administrator. Similarly, those parties who are permitted to access the data are regulated in terms of the permission types accorded to the parties. For a vehicle of a high value, such as a performance or classic vehicle, the system allows for the provenance of the vehicle to be accurately detailed. This is important if the vehicle is to be sold or if the vehicle is to participate in an event or exhibition. In the last mentioned case, the system can accommodate and cater for popularity and value or performance votes to be collected and assessed.

If the vehicle is to be sold then an additional filter module can be used which allows all relevant sale data pertaining to the vehicle to be accessed by a third party upon scanning of the QR code, provided that third party has been authorized by the administrator.

If the vehicle were to be involved in a collision, then for insurance purposes a party involved in the collision could access the QR code and immediately obtain all relevant information pertaining to an insurance claim. Details of the accident or collision can be entered by an authorized party into the data 220 and can then be accessed, as required via, say, the insurance filter 226E.

The system may be linked to a social networking interface and messaging service which enables users to share data on their vehicles with other users on any suitable platform for example one operated by the system itself or on a platform which is publicly available, generally without restriction such as Facebook or You-Tube.

Applications which are vehicle-related can be linked to the system for user selection as required. For example, an application relating to a car washing service can be made available. If the car washing service is employed the application is activated to allow the user's membership of the system to be confirmed and for information pertaining to car washing in general to be made available to the user i.e., such data would form part of the user's profile/permissions. This facility allows separately operated entites which develop or make available innovative applications to be linked to the system of the invention and, vice versa, for the system to drive traffic to such applications and, between such applications.

Inherent in the execution of all of the processes and steps of the system of the invention is a capability to record events on a time and date basis and where appropriate on a geographical basis. Thus, for a given vehicle on a continuous timeline all data of importance or value or otherwise selected, pertaining to that vehicle is recorded automatically and can be accessed or used later for any appropriate reason. This data in effect constitutes a continuous history of everything of import from the manufacture of the vehicle until such time as the use of the system is discontinued.

The invention has been described in some detail in respect of its use pertaining to a vehicle. It is repeated that this particular application is exemplary only for the aforementioned principles can be applied in a variety of ways to any other appropriate object.

The system of the invention can be embellished in various ways to enhance its usability and to increase the functions which it can address.

Figure 5:
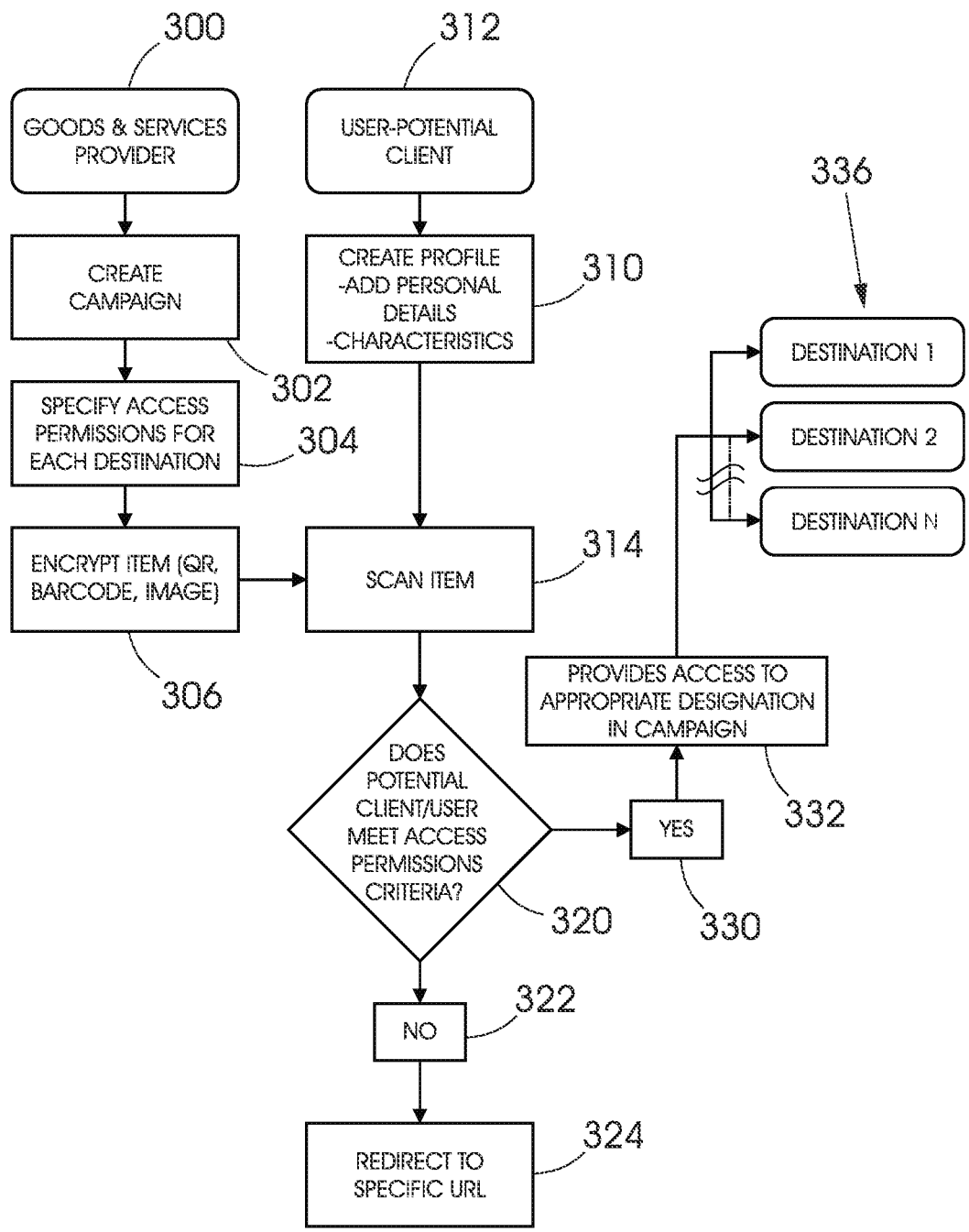
FIG. 5 shows how the method of the invention can be used in a marketing or promotional campaign.

In the preceding description a user, scanning a source, is directed to a destination in accordance with the user's profile. In the detailed example of FIG. 4 the destination is one of several destinations relating to aspects of the vehicle. The principle upon which that technique is modelled can be used for marketing and commercial purposes in what is referred to herein as a campaign. This aspect is explained hereinafter with reference to FIG. 5.

Assume that a goods and services provider 300 initiates a campaign 302. As a part of the campaign access permissions 304 are specified. These permissions are associated with specific users and destinations. For example, a user with permission A is entitled to be directed to a destination X, while a user with permission B would be directed to a destination Y, and so on.

Additionally, an item to be encrypted is chosen. This corresponds to the designation of the source, as referred to hereinbefore, which is to be scanned. A profile 310, which is based on various characteristics, is created for a user 312. When the user scans (step 314) the source 306 the user's profile is evaluated (320) based on the access permission 304 linked with the user. If there is a mismatch (322) the user is directed to a specific URL 324, for example a publicly available destination and is not allowed access to the campaign.

On the other hand if the profile, relevant to the access permission is authenticated (330) the user is allowed access (332) to the campaign and is directed to a destination selected from one of a number of destinations 336 i.e. Destination 1, Destination 2, . . . Destination N.

For example, assume that the provider 300 is a motor dealer who creates a campaign 302 to promote the sale of headlights for a specific vehicle referred to as vehicle X. The user's profile 310 would include, by way of example only, possession of or control over a vehicle, a credit rating, and an address for the user. The access permission databank 304 would record the type X of the vehicle, a user address which must be within a defined distance of the motor dealer, a financial requisite i.e., only a cash deal is accepted.

The source 306 which is scanned may for example be a barcode which is placed on the packaging of the headlight which is the subject of the campaign. Once the barcode is scanned (step 314) a decision is made in step 320 regarding the user's profile data and whether such profile data allows the user to be granted permission (as per the requirement of the access permission database) to be directed to a destination. If favourable the user 312 is allowed to proceed to the appropriate destination 336; assume that this is Destination 2. In this case the user would access all information in Destination 2 which relates to the headlights for vehicle X. Destination 1 might relate to a vehicle A and to a clutchplate for that vehicle, while Destination N might relate to a windscreen for a vehicle T.

In this example the destination 336 is precisely defined as to its subject matter or content, and the permission accorded to each user is dependent at least on the user's profile.

The use of the campaign technique enables a user to be directed to a specific destination which contains all relevant information dealing with the user's enquiry. Information dealing with other aspects of the vehicle is irrelevant and this is not available to the user. Conversely a user who is not interested in headlights for vehicle X would not be directed to the Destination 2. That user would instead be directed to a specific URL 324 which may be of a generalised or non-specific nature dealing with other aspects.

In another example assume that an organisation 300 creates a campaign 302 to provide a series of discounts detailed in the destinations 336 for one or more particular products or services defined in the access permissions databank 304. The user's profile 310 is based, for example, on the user's membership status of the organisation e.g., the length of such membership, the category of membership and participation in the organisation's events. The item which is scanned (step 314) is a QR code which is uniquely related to the campaign and the organisation 300. Once scanning takes place, depending on the user's profile and particular requirement the user may be granted access permission, whereby the user is directed to one of the destinations 336. At that destination the user is notified of, or awarded, a discount, which is dependent on the user's status (profile) for the product or service in question.

In general terms the method of the invention allows for a user to be profiled and granted one or more access permissions which are linked to characteristics of the user. The user can then scan a source which is associated with an object, product or service. The user, if authenticated (e.g., is the user registered or is the user's profile acceptable?) and depending on the user's access permission is then directed to a unique destination which is associated with a category of information, a benefit, an entitlement, or some other facility which is otherwise not available.

The implementation of the method can be controlled by an administrator e.g., computer system which controls requisite access by users to the various destinations.

Each destination may include a category of data related to an object, a service or a product etc. or an application, a commercial proposition or to some other subject matter.

An application of the principles of the invention which has been referred to hereinbefore and which has particular appeal lies in the use of the adaptive technology in the hospitality industry.

For example, referring again to FIG. 5 assume that the goods and services provider 300 is a restaurant chain and that the user/potential client 312 is a person who may visit any of the restaurants in the chain for a meal.

It is open to the chain of restaurants to create a campaign 302 to promote special offerings. Additionally access permissions 304 which allow authorised users to choose from a designated menu may be specified. The use of the campaign procedure 302 and the access permission specification 304 is not essential to this implementation and may, if required, be omitted.

An item is encrypted (306). This conveniently is the incorporation of a QR code, barcode or the like on a menu.

The consumer 312, working in conjunction with the restaurant chain and, for example, in response to a wide-ranging set of questions has created a profile 310 specific to the consumer which deals with food preferences, food consumption, habits, calories per meal, allergies, price preferences and the like.

The user, when visiting any of the restaurants in the chain, is presented with a menu and implements the scanning step 314. If the user's profile complies with the access permission criteria then the user is directed to step 332. For example, referring again to the campaign the restaurant chain might be targeting a promotional exercise at consumers who frequently visit the restaurants. In response special offerings at reduced prices may be made available to these users. This information may be included in the access permission criteria. If the access permission is not used then each potential consumer, according to his/her profile, is directed, as described, to an appropriate destination 336. That destination, in this example, lists a sequence of food offerings in preferred order which are made available to the consumer in accordance with the consumer's profile data.

What is claimed is:

1. A system for controlling the distribution of data to each of a plurality of scanning users via a respective computing device, the system comprising:
   a single scannable source associated with an owner and owner defined subject matter;
   a plurality of digital destinations containing information associated with the owner defined subject matter; and
   wherein a first of the plurality of scanning users is directed to a first of the plurality of digital destinations upon scanning of the single scannable source with their computing device and a second of the plurality of scanning users is directed to a second of the plurality of digital destinations, different from the first of the plurality of digital destinations, upon scanning of the same single scannable source with their computing device.

2. The system of claim 1, further comprising a scanning user profile for each of the plurality of scanning users, the scanning user profile having attributes that are used to determine which of the plurality of digital destinations the scanning user is sent to in response to the scanning of the single scannable source.

3. The system of claim 2, wherein the second scanning user directed to the second of the plurality of digital destination upon scanning of the single scannable source has a profile having attributes that are different than attributes of the profile of the first scanning user directed to the first of the plurality of digital destinations.

4. The system of claim 1, wherein the defined subject matter is one selected from a group consisting of an application, a compilation of data, a product, an object, a service, a commercial proposal, an animate object (a person or an animal), a resource and a motor vehicle.

5. The system of claim 3, wherein the attributes of any one of the plurality of scanning users can be at least one selected from a group consisting of demographic data, interests, titles, age, gender, geographic location, nationality, marital status, occupation, educational qualification and hobbies.

6. The system according to claim 1, wherein the single scannable source comprises one selected from a group consisting of a QR code, an RFID tag, a barcode, an image, and an NFC device.

7. The system according to claim 6, implemented in the field of vehicle technology, wherein the defined subject matter is a defined vehicle, the first scanning user is associated with the defined vehicle and the first scanning user's profile is additionally based at least on attributes of the first scanning user relating to the defined vehicle, wherein each of said plurality of digital destinations is associated with information relating to the defined vehicle, the information relating to the defined vehicle being at least one selected from a group consisting of vehicle service and maintenance data, financial information relating to the vehicle, technical details of the vehicle, insurance details relating to the vehicle and event information.

8. The system according to claim 6, implemented in the medical field wherein the first scanning user is a first medical service provider, the defined subject matter is the card owner as a patient and the single scannable source is uniquely related to the patient, and wherein the first digital destination to which the first scanning user medical service provider is directed includes data and information which is related to a service to be provided to the patient by the first scanning user medical service provider.

9. The system according to claim 8, wherein the second scanning user is a second medical service provider and the second digital destination to which the second scanning user medical service provider is directed includes data and information which is related to a service to be provided to the patient by the second scanning user medical service provider.

10. The system according to claim 9, wherein the first medical service provider and the second medical service provider provide different medical services to the patient, and are directed to different digital destinations including data related to the medical service being provided by the respective medical provider.

11. The system according to claim 1, implemented by a goods or services provider who establishes said plurality of digital destinations and who specifies a respective access permission for a designated digital destination, to be granted to any scanning user of the plurality of users to enable said scanning user to access the designated digital destination, and wherein a scanning user's profile is evaluated, in response to the scanning user scanning the single scannable source, and the scanning user is granted access permission and directed to the designated digital destination only if the scanning user's profile is authenticated for such access to the designated digital destination.

12. The system according to claim 11, wherein if the scanning user's profile is not authenticated, the scanning user is not granted access permission to the designated digital destination and is directed to another digital destination informing them of their lack of authentication.

13. The system according to claim 2, implemented in the hospitality industry, wherein each of the plurality of scanning users is a potential consumer of food or beverage offerings and wherein the scanning user's profile is dependent, at least, on consumption preferences of the user, the single scannable source is associated with a menu which details food or beverage offerings and, in response to the scanning, the first of the plurality of scanning users is directed to a digital destination which reflects foods or beverages, available to the first of the plurality of scanning users which are dependent on the first scanning user's profile and the second of the plurality of scanning users, in response to the scanning, is directed to another digital destination that reflects foods or beverages available to the second of the plurality of scanning users and which is dependent on the second scanning user's profile.

* * * * *